United States Patent [19]

Burton et al.

[11] Patent Number: 4,650,887

[45] Date of Patent: Mar. 17, 1987

[54] METHOD OF PREPARATION OF COMPOUNDS CONTAINING PERFLUOROALKYL GROUPS

[75] Inventors: Donald J. Burton, Iowa City; Denise M. Wiemers, West Branch; Jerome C. Easdon, Iowa City, all of Iowa

[73] Assignee: University of Iowa Research Foundation, Iowa City, Iowa

[21] Appl. No.: 809,291

[22] Filed: Dec. 16, 1985

Related U.S. Application Data

[62] Division of Ser. No. 651,163, Sep. 17, 1984, Pat. No. 4,582,921.

[51] Int. Cl.$^4$ .............................................. C07F 1/08
[52] U.S. Cl. .................................................... 556/112
[58] Field of Search ........................................ 556/112

[56] References Cited

U.S. PATENT DOCUMENTS 3,401,186  9/1968  Müller et al. ...................... 556/112
3,549,678  12/1970  Muller et al. ...................... 556/112
3,700,710  10/1972  Mottus et al. .................. 556/112 X
3,809,726  5/1974  Horowitz et al. .............. 556/112 X

OTHER PUBLICATIONS

Chemical Abstracts 94 174487v (1981).

Primary Examiner—Helen M. S. Sneed
Attorney, Agent, or Firm—Zarley, McKee, Thomte, Voorhees & Sease

[57] ABSTRACT

The basic single step process for preparing trifluoromethyl organocadmium and zinc compounds from difluorodihalomethane is disclosed. The prepared trifluoromethyl compound may be used to add the trifluoromethyl to a variety of organic structures in a trifluoromethylating reaction. Among the structures included are aromatic compounds, halo olefins, allylic compounds, acetylenic compounds and acyl halides.

11 Claims, No Drawings

METHOD OF PREPARATION OF COMPOUNDS CONTAINING PERFLUOROALKYL GROUPS

This is a division of application Ser. No. 651,163, filed Sept. 17, 1984.

BACKGROUND OF THE INVENTION

Many organic compounds containing the trifluoromethyl group are extremely valuable compounds, useful in a variety of ways. For example, many agricultural chemicals which are herbicides, pesticides, and fungicides, contain the trifluoromethyl group attached to an aromatic ring. Perhaps one of the more famous is a herbicide sold under the trademark "Treflan". In addition, some well known solvents have the trifluoromethyl moiety, as well as certain valuable chemical intermediates. In sum, there is a very real and continuing need for cheap, inexpensive and economic ways of introducing the trifluoromethyl group into both pharmaceutically active, and agricultural chemically active compounds.

In the past, the synthetic routes for such compounds have been laborious. In particular, fluorinating agents used to prepare trifluoromethyl containing compounds have all been a compound which in fact already contained the trifluoromethyl group such as trifluoromethyl iodide, and bis(trifluoromethyl)mercury. These compounds are expensive, and not readily commercially available.

Contrasted with the expensive and difficult methods to obtain trifluoromethyl compounds, there are many cheap, commercially available difluorodihalomethanes, such as $CF_2Cl_2$, $CF_2BrCL$, and $CF_2Br_2$. However, no one has heretofore ever been able to achieve a direct synthesis of a trifluoromethyl organo metallic from a difluorodihalo compound.

Accordingly, it is a primary objective of the present invention to prepare trifluoromethyl organometallics from commercially available difluorodihalomethanes, such as dichlorodifluoromethane, chlorobromodifluoromethane, and dibromodifluoromethane.

Yet another objective of the present invention is to prepare trifluoromethyl organocadmium and zinc compounds from difluorodihalomethanes in a direct single step synthesis.

An even further objective of the present invention is to prepare stable trifluoromethyl copper reagents which are useful in further synthetic reactions to allow introduction of trifluoromethyl groups to other compounds.

A further objective of the invention is to prepare trifluoromethyl organometallic compounds of cadmium and zinc and copper which can be conveniently used to introduce the trifluoromethyl moiety to an olefinic derivative.

A further objective of the present invention is to prepare trifluoromethyl organometallic compounds of cadmium and zinc and copper which can be conveniently used to introduce the trifluoromethyl moiety into an aromatic compound.

A further objective of the present invention is to prepare trifluoromethyl organometallic compounds of cadmium and zinc and copper which can be conveniently used to introduce the trifluoromethyl moiety to an unsaturated organic compound, such as an acetylenic or an allylic compound.

A further objective of the present invention is to prepare trifluoromethyl organometallic compounds of cadmium and zinc and copper which can be conveniently used to introduce the trifluoromethyl moiety to an acyl derivative.

A further objective of the present invention is to prepare trifluoromethyl organometallic compnds of cadmium and zinc and copper which can be conveniently used to introduce the trifluoromethyl moiety for the preparation of other trifluoromethyl organometallics via metathasis reactions.

A still further objective is to prepare either directly or indirectly, perfluoroalkyl organometallic compounds of copper and other transition metals which can then be conveniently used to introduce a perfluoroalkyl group into an organic compound.

The method and manner of accomplishing each of the above objectives will become apparent from the detailed description of the invention which will follow hereinafter.

SUMMARY OF THE INVENTION

A process of preparing trifluoromethyl organometallics with cadmium, zinc and copper from commercially available difluorodihalomethanes is described. The process represents the first ever direct synthesis of trifluoromethyl organometallics such as cadmium, zinc and copper compounds from difluorodihalomethanes. In addition, the cadmium and zinc trifluoromethyl organometallics prepared can be used to prepare a stable trifluoromethyl copper compound. All of the compounds are useful in a wide variety of synthetic reactions to introduce the trifluoromethyl moiety to the desired positions on aromatics, such as aromatic halides, olefins, particularly halo olefins, and acetylenic and allylic unsaturated compounds, and acyl derivatives as well. In a preferred process, the reaction is conducted in the presence of dimethylformamide.

DETAILED DESCRIPTION OF THE INVENTION

In accordance with the broadest aspect of this invention which involves preparing trifluoromethyl organo cadmium and zinc compounds, a compound of the formula $CF_2XY$, wherein X and Y are halogens, is reacted preferably with a metal selected from the group consisting of cadmium and zinc to provide a trifluoromethyl metal halide. X and Y may be the same or different, and are selected from the group of chlorine, bromine and iodine. Suitable compounds of this class include dichlorodifluoromethane, dibromodifluoromethane, and bromochlorodifluoromethane. The compound is reacted preferably with cadmium or zinc in order to provide stable compounds in a direct synthetic reaction represented by the following equation:

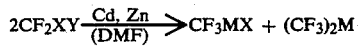

X = Br, Cl, I
Y = Br, Cl, I
DMF = Dimethylformamide

The abbreviation "DMF" refers to dimethylformamide. It is currently not believed that dimethylformamide is critical, but the reaction must be conducted in the presence of an aprotic solvent since the cadmium reagent is hydrolyzed by water. Amongst those known to be suitable are dimethylformamide which is strongly preferred, methyl formamide, acetonitrile, and N-methylpyrolidine, and dimethylsulfide. The reaction is direct and will allow preparation in yields of 90–95%, of the trifluoromethyl cadmium or zinc reagent. The reaction with the cadmium is faster than with zinc and at times is over in as little as a few minutes at room temperature. The reaction with the zinc compounds may take somewhat longer, and in the past has been run from time to time of from between eight and ten hours at 60° C.–70° C. Thus, in summary, the reaction will occur at temperatures ranging from about room temperature, up to about 75° C., preferably for the zinc reaction from about 50° C. to about 75° C., and for the cadmium reaction may be at any temperature from room temperature up to about 75° C. The reaction time will run from a few minutes to a few hours. The trifluoromethyl cadmium or zinc reagent is stable and can be used for a variety of syntheses as described below.

The trifluoromethyl cadmium or zinc reagent prepared in accordance with this reaction can be used in an in situ preparation for introduction of the trifluoromethyl group into a variety of compounds.

In certain instances, because of its activity, it is also desirable to prepare trifluoromethyl copper reagents of the formula $CF_3Cu$. It is possible to prepare trifluoromethyl copper directly from the reaction of difluorodihalomethanes and copper; however, the $CF_3Cu$ undergoes chain elongation to form longer chain perfluoroalkyl copper reagents, unless the trifluoromethyl copper is trapped in situ. However, the cadmium and zinc reagents can be converted to a stable $CF_3Cu$, which itself is useful for trifluoromethylation. The trifluoromethyl cadmiun or zinc reagent is reacted with a copper salt of the formula CuZ, wherein Z represents any solvent soluble anion which may be selected from, for example, the group of nitrate, phosphate, halides, including bromide, chloride and iodide, sulfate, acetate, trifluoroacetate, cyanide and the like. It is not critical what the anion is, only that it be solvent soluble for ease of introduction of the organo-copper into the reaction system. Again, the reaction should be conducted in the presence of an aprotic solvent and in fact, may be conducted in situ in the same reaction vessel as the earlier preparation of the trifluoromethyl cadmium or zinc reagent.

Since the copper trifluoromethyl reagent can have stability problems in its preparation, it is desirable to run this reaction at temperatures of less than 0° C. A flask cooled with dry ice—isopropyl alcohol has been found to be satisfactory, with temperatures ranging from about 0° C. to −70° C. Ideally, temperatures within the range of −40° C. to −70° C. have been found satisfactory.

Other trifluoromethyl or perfluoroalkyl organometallics such as the trifluoromethyl tin reagent can be prepared via an analogous reaction of the difluorodihalomethanes directly with the metal. In addition, other trifluoromethyl organometallics such as palladium, rhodium, platinum, gold, cobalt, mercury or silver can be prepared by the indirect metathesis reaction of the appropriate metal salt with the trifluoromethyl cadmium reagent.

As heretofore stated, trifluoromethyl compounds have been generally prepared by substitution on fluorine for halogens such as bromine, chlorine, and iodine. Now, for the first time, they are available from a direct synthetic route from cheap and available difluorodihalomethanes.

The prepared trifluoromethyl reagent may be reacted in situ in many reactions in order to introduce the trifluoromethyl group into an aromatic ring, into an olefin at the point of unsaturation, or into an acetylenically or allylically unsaturated compound, or into an acyl derivative. The number of reactions which can be performed are almost limitless, but generally lower aromatics, lower $C_2$ to $C_{12}$ olefins, particularly halo olefins, and lower $C_2$ to $C_{12}$ acetylenically or allylically unsaturated compounds, and acyl derivatives can be conveniently used. All are illustrated in the examples.

The following examples are offered to further illustrate, but not necessarily limit the process and products of this invention.

EXAMPLE 1

Preparation of Trifluoromethyl Cadmium from Dibromodifluoromethane

A three-neck 250 ml round bottom flask equipped with stopper, septum, magnetic stirbar and nitrogen tee was charged with 50 ml DMF and 22.4 g (0.2 moles) activated cadmium. The $CF_2Br_2$ (9.1 ml, 0.1 moles) was added via a pre-cooled syringe. An exothermic reaction occurred and the solution turned dark brown. The reaction mixture was stirred for two hours at room temperature, then filtered through a medium-fritted schlenk funnel under nitrogen. The precipitate ($CdBr_2$) was washed with 10–15 ml DMF. The resulting filtrate was utilized in subsequent reactions. Typical yields of $CF_3CdX$ were 90–95% based on 2 moles of the methane being converted to 1 mole of cadmium reagent.

EXAMPLE 2

Preparation of Trifluoromethyl Cadmium from Bromochlorodifluoromethane

The $CF_2BrCl$ was measured into a 15 ml graduated tube via a dry ice/IPA condenser (8.6 ml, 0.10 moles). Phosphorus pentoxide was added to the methane. The $CF_2BrCl$ was transferred to a similarly equipped flask as above except a dry ice/IPA condenser was added. The resulting exothermic reaction yields a dark brown solution which was filtered and washed as before. Typical yields were 90–95%.

EXAMPLE 3

Preparation of Trifluoromethyl Cadmium from Dichlorodifluoromethane

A 300 ml sealed tube was charged with Cd(22.4 g, 0.20 mole), $CF_2CL_2$ (8.1 ml, 0.10 mole) and 50 ml DMF. The reaction tube was heated to 80° C. for 24 hours. The resulting reaction mixture was pressure filtered through a medium fritted schlenk funnel and the precipitate was washed with 10–15 ml DMF.

EXAMPLE 4

Preparation of Trifluoromethyl Copper from the Trifluoromethyl Cadmium Solution Prepared from $CF_2BrCl$ The reaction mixture containing $CF_3CdX$ prepared previously was cooled to −70° C. with a dry ice/IPA bath. Cuprous bromide (7.2 g, 0.5 moles) was added to the cooled flask and warmed slightly (−50° C.) for efficient stirring. The reaction mixture was used at this temperature in subsequent reactions. At higher temperatures the CF₃Cu decomposes. Typical yields for CF₃Cu (based on CF₃Cd) are 90–95%.

EXAMPLE 5

Utilization of the Trifluoromethyl Copper Solution with Allylic Halides

Typical procedure:

The CF₃Cu solution was cooled to −70° C. and the allyl halide (0.03 moles) was added. The solution was slowly warmed to room temperature. The solution was stirred at room temperature for 2–4 hours, steam distillation followed by fractional distillation resulted in isolated yields of 50–75%.

EXAMPLE 6

Formation of CF₃X; X=I, D

Typical procedure:

The solution containing CF₃CdBr is cooled to 0° C. with an ice bath and I₂ or D₂O is slowly added. Flash distillation followed by trap to trap distillation resulted in CF₃I (24%) and CF₃D (34%).

EXAMPLE 7

Formation of CF₃Ar

The solution containing the cadmium reagent was utilized. An equal volume of HMPA (Hexamethylphosphoramide) was added to the cadmium reagent solution. Cuprous bromide (7.2 g, 0.05 moles) was added at room temperature. The aromatic compound (0.20 moles) was added to the solution and was heated to 60°–70° C. for four hours. The reaction mixture was steam distilled, the organic layer separated and fractionally distilled. Typical yields (based on aromatic halide) were 60–80%.

EXAMPLE 8

Formation of Trifluoromethylated Olefins

Typical procedure:

The solution containing the copper reagent at −70° C. was utilized in the formation of trifluoromethylated olefins. The vinyl halide was added to the copper reagent at −70° C. and slowly allowed to warm to room temperature. The reaction mixture was flash distilled. The flash distillate was washed with water and the organic layer separated. The olefin was fractionally distilled. Typical yields (based on vinyl halide) were 40–69%.

EXAMPLE 9

Preparation of Perfluoroethyl Copper from Trifluoromethylcopper

The copper reagent prepared at −70° C. was slowly allowed to warm to room temperature. Perfluoroethyl copper was obtained in 90% yield based on trifluoromethyl copper. A solution of I₂ in DMF was added to the ethyl copper reagent. The reaction mixture was flash distilled followed by trap to trap distillation resulted in a 65% isolated yield of perfluoroethyl iodide.

EXAMPLE 10

Preparation of Trifluoromethyl Zinc from Bromochlorodifluoromethane

A three-necked 100 ml round bottomed flask, equipped with a dry ice/IPA condenser, magnetic stirbar, septum and stopper was charged with 50 ml of DMF and activated zinc (6.3 g, 0.10 moles). The methane (8.6 ml, 0.05 moles) was added via the dry ice/IPA condenser and the solution was heated for 8–10 hours at 65°–70° C. The resulting solution was filtered through a medium-fritted schlenk funnel. The yield of the trifluoromethyl zinc was 50–60% based on starting methane.

EXAMPLE 11

Formation of Trifluoromethyl Ketones from the Trifluoromethyl Zinc

The trifluoromethyl zinc reagent was cooled to −20-(−30° C.) and the acid chloride was added. The reaction mixture was warmed to room temperature and allowed to stir overnight. Flash distillation followed by addition of water and separation of the organic layer gave a yield (40%) of the trifluoromethylated ketone.

EXAMPLE 12

Preparation of Trifluoromethyl Aromatics

$$Cu + CF_2BrX + ArI \xrightarrow{DMF} Ar(CF_2)_nCF_3$$

(X = Cl, Br)

| Materials | |
|---|---|
| Cu | 1.91 g. (30 mmoles) |
| CF₂BrX | 0.91 ml (X = Br), 0.86 ml (X = Cl) (10 mmoles) |
| ArI | 5 mmoles |
| Dimethylformamide (DMF) | 10 ml. |

Procedure:

The copper metal was weighed into a 25 ml. round bottom flask which was equipped with a septum. A dry ice/acetone condenser was placed on the flask and the apparatus was maintained under nitrogen atmosphere. DMF, aromatic iodide and CF₂BrX were added to the flask. The reaction mixture was stirred and heated with an oil bath until it appears that all of the copper metal has been converted to copper halide.

Yields (¹⁹F-NMR) are usually greater than 60%, based upon the amount of aromatic iodide converted to perfluoroalkyl aromatics. A mixture of perfluoroalkyl aromatics was generally obtained, although the trifluoromethylated aromatic is the major product. The highest proportion of the trifluoromethyl product was obtained utilizing CF₂BrCl at a temperature of 85° C.

The chain extension can be suppressed by the addition of fluoride ion (CsF, KF). This gave mixtures with much larger proportions of the trifluoromethylated aromatic compound. Less copper metal was consumed, although the reaction time was longer.

EXAMPLE 13

Preparation of Perfluoroalkyl Copper Reagents

$$Cu + CF_2BrX \xrightarrow{DMF} CF_3(CF_2)_nCu$$

(X = Cl, Br)

| Materials | |
|---|---|
| Cu | 1.91 g. (30 mmoles) |
| CF₂BrX | 0.91 ml (X = Br), 0.86 ml (X = 0), (10 mmole) |
| Dimethylformamide (DMF) | 10 ml. |

Procedure:

The finely divided copper metal was weighed into a 25 ml. round bottom flask which was equipped with a septum. A dry ice/acetone condenser was placed on the flask and the apparatus was equipped with an oil bubbler and maintained under a nitrogen atmosphere. DMF and $CF_2BrX$ were added to the flask. The reaction mixture was stirred and heated with an oil bath until it appears that all of the copper metal has been converted to copper halide.

Typical yields ($^{19}$F-NMR) are around 60%. The products obtained were a mixture of perfluoroalkyl copper reagents. The chain lengths ranged from 2 to 17 carbons (detected by GC/MS), but the major products were F-ethyl, F-propyl and F-butyl copper. The product distribution was a function of temperature and X. The best proportions of F-ethyl copper (~80%) was obtained using $CF_2BrCl$ and 70° C. Using $CF_2Br_2$ at 85° C. gives the product distribution with the highest proportion of F-butyl copper (~80%).

EXAMPLE 14

Preparation of Perfluoroethyl Aromatic Compounds

The perfluoroethyl copper was prepared as previously described. An aromatic iodide was added to this solution and heated to 60°–70° C. for four to six hours. After the reaction was complete, the reaction mixture was steam distilled. The organic and aqueous layers were separated and the aqueous layer extracted wity (3×20 ml) pentane. The pentane layer was dried over anhydrous $MgSO_4$. The pentane was either distilled or removed under reduced pressure depending on the property of the product.

EXAMPLE 15

Preparation of Trifluoromethyl Tin Halide

A three-neck 50 ml. round bottom flask equipped with stopper, septum, magnetic stirbar and nitrogen tee was charged with 20 ml. DMF and 11.9 g (0.1 mole) Sn. The $CF_2Br_2$ (4.6 ml, 0.05 mole) was added via precooled syringe. An exothermic reaction occurred and the reaction mixture turned dark brown. Subsequent analysis confirmed the presence of $(CF_3)_n$ Sn X, wherein n=1-4 or in other words, $(CF_3)$ $SnX_3$, $(CF_3)_2$ $SnX_2$, $(CF_3)_3$ SnX, $(CF_3)_4$ Sn.

EXAMPLE 16

Preparation of Various Organometallics from $CF_3CdX$

A solution of $CF_3CdX$ in DMF was reacted with each of the following metal halide complexes to yield the corresponding trifluoromethyl organometallic derivative.

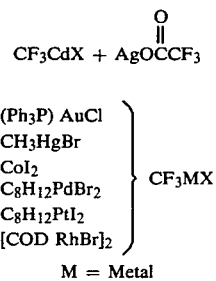

What is claimed is:

1. A method of producing stable trifluoromethyl copper reagent of the formula $CF_3Cu$ from a difluoromethyl halide of the formula $CF_2XY$, comprising:

reacting a compound of the formula $CF_2XY$, wherein X and Y are halogens, with a metal selected from the group of cadmium and zinc to provide a trifluoromethyl metal halide of the formula $CF_3MX$ wherein M is a metal selected from the group of cadmium and zinc; and thereafter reacting said trifluoromethyl compound of the formula $CF_3MX$ with a copper salt of the formula CuZ, wherein Z is any reaction solvent soluble anion to provide said stable trifluoromethyl copper reagent.

2. The method of claim 1 wherein said reaction is conducted in the presence of an aprotic solvent.

3. The method of claim 2 wherein said solvent is selected from the group consisting of methylformamide, dimethylformamide, acetonitrile, N-methylpyrrolidine and dimethylsulfide.

4. The method of claim 3 wherein said solvent is dimethylflormamide.

5. The method of claim 1 wherein X is chloride.

6. The method of claim 1 wherein X is bromide.

7. The method of claim 1 wherein X is iodine.

8. The method of claim 1 wherein Z is a halide.

9. The method of claim 1 wherein said reaction is conducted at less than 0° C.

10. The method of claim 1 wherein said reaction is conducted at a temperature of from about −70° C. to about 0° C.

11. The method of claim 9 wherein said reaction is conducted at a temperature of from about −40° C. to about −70° C.

* * * * *